(12) United States Patent
Miyakawa et al.

(10) Patent No.: US 12,385,935 B2
(45) Date of Patent: Aug. 12, 2025

(54) ELECTROLYTE ANALYZER

(71) Applicant: HITACHI HIGH-TECH CORPORATION, Tokyo (JP)

(72) Inventors: Takushi Miyakawa, Tokyo (JP); Ryota Watanabe, Tokyo (JP); Yuichi Iwase, Tokyo (JP); Takahiro Kumagai, Tokyo (JP); Masafumi Miyake, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 336 days.

(21) Appl. No.: 18/015,971

(22) PCT Filed: Mar. 11, 2021

(86) PCT No.: PCT/JP2021/009801
§ 371 (c)(1),
(2) Date: Jan. 13, 2023

(87) PCT Pub. No.: WO2022/014096
PCT Pub. Date: Jan. 20, 2022

(65) Prior Publication Data
US 2023/0288439 A1    Sep. 14, 2023

(30) Foreign Application Priority Data
Jul. 16, 2020  (JP) .................................. 2020-122088

(51) Int. Cl.
*G01N 35/00* (2006.01)
*G01N 35/04* (2006.01)

(52) U.S. Cl.
CPC ....... *G01N 35/00732* (2013.01); *G01N 35/04* (2013.01); *G01N 2035/00891* (2013.01); *G01N 2035/0462* (2013.01)

(58) Field of Classification Search
CPC ............. G01N 35/00732; G01N 35/04; G01N 2035/00891; G01N 2035/0462
(Continued)

(56) References Cited

U.S. PATENT DOCUMENTS 4,649,028 A * 3/1987 Kaltenbach ........ G01N 35/1097
137/625.13
2012/0228158 A1  9/2012 Tonomura

FOREIGN PATENT DOCUMENTS

JP     2008190958 A  *  8/2008
JP     2011-33425 A     2/2011
(Continued)

OTHER PUBLICATIONS

Translation of JP-2008190958-A (Year: 2008).*
(Continued)

*Primary Examiner* — Nathaniel T Woodward
(74) *Attorney, Agent, or Firm* — MATTINGLY & MALUR, PC

(57) ABSTRACT

There is provided an electrolyte analyzer that can appropriately replace consumable items while more exerting analysis processing performances than a conventional electrolyte analyzer does. An electrolyte analyzer includes a plurality of analysis chambers 50 having ISE electrodes 1 configured to measure the concentration of the electrolyte of a sample and a controller 29 configured to control operations in the electrolyte analyzer 100 including the analysis chambers 50. The ISE electrodes 1 of the plurality of analysis chambers 50 analyze the same analysis items. The controller 29 selects an analysis chamber 50 used for measurement from the plurality of analysis chambers 50 corresponding to the remaining measurable numbers of a plurality of ISE electrodes 1 and measurement request status.

7 Claims, 10 Drawing Sheets

(58) Field of Classification Search
USPC .................................................. 73/864.81
See application file for complete search history.

(56) References Cited

FOREIGN PATENT DOCUMENTS

| | | |
|---|---|---|
| JP | 2011-112489 A | 6/2011 |
| JP | 2012-189405 A | 10/2012 |
| JP | 2015-148500 A | 8/2015 |

OTHER PUBLICATIONS

International Preliminary Report on Patentability received in corresponding International Application No. PCT/JP2021/009801 dated Jan. 19, 2023.
International Search Report of PCT/JP2021/009801 dated May 18, 2021.

* cited by examiner

FIG. 4

| ANALYSIS UNIT 1 | TARGET | REMAINING NUMBER OF TIMES OF MEASUREMENT | EXPIRATION DATE |
|---|---|---|---|
| ANALYSIS CHAMBER 1 | $Na^+$ | 20 | 2020/06/20 |
| | $K^+$ | 25 | 2020/06/20 |
| | $Cl^-$ | 21 | 2020/06/20 |
| ANALYSIS CHAMBER 2 | $Na^+$ | 15 | 2020/07/04 |
| | $K^+$ | 10 | 2020/07/04 |
| | $Cl^-$ | 19 | 2020/07/04 |

CLOSE

FIG. 7

ANALYSIS UNIT 1

| | | REMAINING MEASURABLE NUMBER OF ELECTRODE | | | EXPIRATION DATE | REMAINING LIQUID AMOUNT OF REAGENT / EXPIRATION DATE | | |
|---|---|---|---|---|---|---|---|---|
| | | Na⁺ | K⁺ | Cl⁻ | | INTERNAL STANDARD SOLUTION | REFERENCE ELECTRODE SOLUTION | DILUENT |
| ☐ | ANALYSIS CHAMBER 1 | 20 | 25 | 21 | 2020/06/20 | 40 2020/06/30 | 65 2020/06/25 | 89 2020/07/05 |
| ☐ | ANALYSIS CHAMBER 2 | 15 | 10 | 19 | 2020/07/04 | 60 2020/08/01 | 52 2020/08/01 | 93 2020/08/01 |

[APPLY] [CLOSE]

FIG. 9

| | | ANALYSIS UNIT 1 | ANALYSIS UNIT 2 | ANALYSIS UNIT 3 | ANALYSIS UNIT 4 | ANALYSIS UNIT 5 |
|---|---|---|---|---|---|---|
| REMAINING MEASURABLE NUMBER OF ELECTRODE | Na⁺ | 30 | 5 | 33 | 22 | 26 |
| | K⁺ | 26 | 40 | 10 | 18 | 29 |
| | Cl⁻ | 40 | 44 | 9 | 19 | 23 |
| EXPIRATION DATE | | 32 | 35 | 12 | 15 | 28 |
| | | 2020/08/20 | 2020/07/31 | 2020/08/06 | 2020/06/20 | 2020/08/08 |
| REMAINING LIQUID AMOUNT OF REAGENT | INTERNAL STANDARD SOLUTION | 50 | 60 | 110 | 6 | 70 |
| | REFERENCE ELECTRODE SOLUTION | 93 | 74 | 99 | 78 | 45 |
| | DILUENT | 120 | 67 | 5 | 105 | 75 |
| | | 63 | 70 | 6 | 7 | 37 |
| | | 81 | 54 | 120 | 7 | 74 |
| | | 118 | | | 98 | 40 |
| REAGENT EXPIRATION DATE | INTERNAL STANDARD SOLUTION | 2020/07/01 | 2020/08/16 | 2020/09/01 | 2020/07/02 | 2020/08/14 |
| | REFERENCE ELECTRODE SOLUTION | 2020/07/10 | 2020/08/06 | 2020/08/20 | 2020/07/10 | 2020/07/28 |
| | DILUENT | 2020/07/04 | 2020/08/05 | 2020/08/31 | 2020/07/01 | 2020/08/12 |
| | | 2020/07/14 | | | 2020/07/08 | 2020/09/10 |
| | | | | | 2020/08/19 | 2020/08/03 |
| | | | | | 2020/09/06 | 2020/09/08 |
| | | | | | 2020/06/30 | 2020/08/01 |
| | | | | | 2020/07/07 | |

[ CLOSE ]   [ APPLY ]

FIG. 10

| | | ANALYSIS UNIT 1 | | ANALYSIS UNIT 2 | | ANALYSIS UNIT 3 | | ANALYSIS UNIT 4 | | ANALYSIS UNIT 5 | |
|---|---|---|---|---|---|---|---|---|---|---|---|
| | | CHAMBER 1 | CHAMBER 2 | CHAMBER 1 | CHAMBER 2 | CHAMBER 1 | CHAMBER 2 | CHAMBER 1 | CHAMBER 2 | CHAMBER 1 | CHAMBER 2 |
| REMAINING MEASURABLE NUMBER OF ELECTRODE | Na⁺ | 30 | 26 | 5 | 40 | 33 | 10 | 22 | 18 | 26 | 27 |
| | K⁺ | 31 | 40 | 6 | 44 | 38 | 9 | 20 | 19 | 29 | 23 |
| | Cl⁻ | 30 | 32 | 3 | 35 | 36 | 12 | 27 | 15 | 28 | 20 |
| EXPIRATION DATE | | 2020/08/20 | 2020/09/18 | 2020/06/30 | 2020/07/31 | 2020/08/06 | 2020/07/07 | 2020/06/20 | 2020/07/11 | 2020/08/08 | 2020/08/08 |
| REMAINING LIQUID AMOUNT OF REAGENT | INTERNAL STANDARD SOLUTION | 50 | 93 | 60 | 74 | 110 | 6 | 78 | 98 | 70 | 45 |
| | REFERENCE ELECTRODE SOLUTION | 63 | 120 | 62 | 67 | 99 | 5 | 7 | 105 | 75 | 37 |
| | DILUENT | 81 | 118 | 54 | 70 | 120 | 6 | 7 | 98 | 74 | 40 |
| REAGENT EXPIRATION DATE | INTERNAL STANDARD SOLUTION | 2020/07/01 | 2020/08/04 | 2020/09/01 | 2020/07/02 | 2020/07/10 | 2020/08/14 | 2020/07/28 |
| | REFERENCE ELECTRODE SOLUTION | 2020/07/10 | 2020/07/14 | 2020/08/06 | 2020/08/20 | 2020/07/01 | 2020/07/08 | 2020/09/10 | 2020/08/03 |
| | DILUENT | 2020/07/01 | 2020/07/04 | 2020/08/05 | 2020/08/31 | 2020/06/30 | 2020/07/07 | 2020/09/06 | 2020/08/01 |

APPLY    CLOSE

ELECTROLYTE ANALYZER

TECHNICAL FIELD

The present invention relates to an electrolyte analyzer.

BACKGROUND ART

As an example of an electrolyte measurement device that is capable of accurately performing measurement with no complication of the configuration of the device, with no increase in a sample solution, regardless of the concentration of a sample solution, Patent Literature 1 describes an electrolyte measurement device including a measurement unit that measures electromotive forces of a standard solution and a sample solution using an electrode unit, a dilution chamber that dilutes the sample solution with a diluent to generate a sample solution, a sample supply unit that supplies the sample solution to the dilution chamber, a diluent supply unit that supplies a diluent to the dilution chamber, a standard solution supply unit that supplies a standard solution to the dilution chamber, a measurement solution supply unit that supplies the standard solution and the sample solution from the dilution chamber to the electrode unit, and a control unit that controls the standard solution and the sample solution to be alternately supplied from the dilution chamber to the electrode unit and that controls the diluent to be supplied by a predetermined amount to the dilution chamber for discharge before the sample solution is generated.

CITATION LIST

Patent Literature

Patent Literature 1: Japanese Unexamined Patent Application Publication No. 2012-189405

SUMMARY OF INVENTION

Technical Problem

The electrolyte analyzer as set forth in Patent Literature 1 is a device that measures the concentration of a specific electrolyte (sodium (Na), potassium (K), chlorine (Cl), and the like) contained in an electrolytic solution such as human blood and urine, and measures concentrations with an ion selective electrode.

As a typical measurement method for electrolyte concentrations, the following flow type is mainly used. A blood serum that is an electrolytic solution is directly supplied to an ion selective electrode or a sample solution diluted with a diluent is supplied to the ion selective electrode, and the potential across the electrolytic solution and a reference electrode solution. Subsequently, or prior to the above-described measurement, a standard solution is supplied to the ion selective electrode to similarly measure the potential across the standard solution and the reference electrode solution, and the electrolyte concentration of the sample solution is calculated from the potential level between the two solutions.

In the flow type electrolyte analyzer, the ion selective electrode is used as a consumable item in addition to reagents such as a diluent, a standard solution, and a reference electrode solution, and the replacement work of these consumable items is performed by a user.

In the conventional electrolyte analyzer, although the measurable number of times and the expiration date are defined in consumable items such as an electrode and a reagent, the management of the measurable number of times or the expiration date is rarely performed except the reagent.

Moreover, in an electrolyte analyzer including a plurality of analysis chambers, matching of remaining measurable numbers between the analysis chambers is extremely rare, and many different cases occur. Regardless of such situations, in regard to the analysis chamber to be used, appropriate allocation has not been performed such as simple alternate measurement, or measurement from one analysis chamber all the time.

Therefore, it has become apparent from investigation by the present inventors that cases occur where the replacement frequency of consumable items by the user increases more than necessary or the maximum processing performance fails to be exerted.

The present invention has been made in view of such problems. It is an object to provide an electrolyte analyzer that is capable of appropriately replacing consumable items while exerting the analysis processing performance as compared with a conventional electrolyte analyzer.

Solution to Problem

The present invention includes a plurality of units that solve the problems. An example is an electrolyte analyzer that analyzes electrolyte concentration of a sample, the electrolyte analyzer including: a plurality of analysis chamber having consumable items that measure concentration of an electrolyte of the sample; and a control unit configured to control operations in the electrolyte analyzer including the analysis chamber. In the electrolyte analyzer, a plurality of analysis chamber shares a dispensing mechanism configured to dispense the sample to the analysis chamber, the consumable items of the plurality of analysis chambers analyze equal analysis items, the control unit selects an analysis chamber used for measurement from the plurality of analysis chambers corresponding to remaining measurable numbers of the plurality of consumable items and measurement request status, and when a plurality of the dispensing mechanisms is included, the control unit selects the dispensing mechanism used for dispensing and the analysis chamber used for measurement corresponding to remaining measurable numbers and measurement request status of the plurality of analysis chambers.

Advantageous Effects of Invention

According to the present invention, it is possible to appropriately replace consumable items while exerting the analysis processing performance as compared with a conventional electrolyte analyzer. Problems, configurations, and effects except ones described above will be apparent from embodiments below.

BRIEF DESCRIPTION OF THE DRAWINGS

FIG. 4 is a diagram showing a screen that manages remaining measurable numbers displayed on the display device of the electrolyte analyzer according to the first embodiment;

FIG. 7 is a diagram showing a screen that is displayed on the display device of the electrolyte analyzer according to the first embodiment and that selects an analysis chamber used in priority;

FIG. 9 is a diagram showing a screen that is displayed on the display device of the electrolyte analyzer according to the second embodiment and that selects a dispensing mechanism used in priority; and FIG. 10 is a diagram showing a screen that is displayed on the display device of the electrolyte analyzer according to the second embodiment and that selects an analysis chamber used in priority.

DESCRIPTION OF EMBODIMENTS

Figure 1:
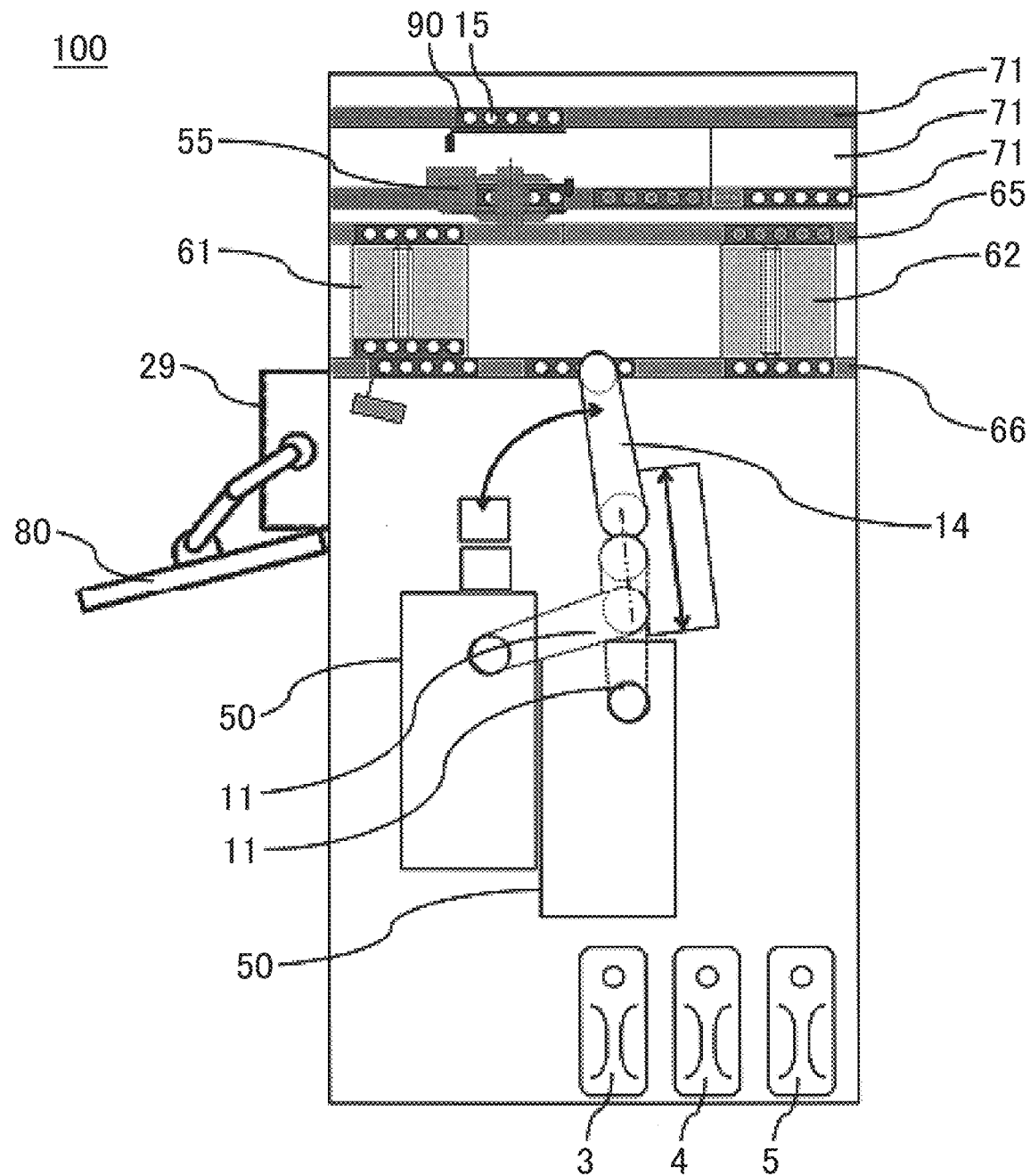
FIG. 1 is a diagram showing the overall structure of an electrolyte analyzer according to a first embodiment of the present invention.

In the following, embodiments of an electrolyte analyzer according to the present invention will be described with reference to the drawings. Note that in the drawings used in the present specification, the same or the corresponding components are designated with the same, or similar reference signs, and a duplicate description of these components is sometimes omitted.

Moreover, in the embodiments shown below, the electrolyte analyzer will be described in the case in which a device that analyzes electrolyte items is constituted of one device or a plurality of devices. However, the device configuration is not limited to these forms, and the device can be mounted on the automatic analyzer. Examples of the automatic analyzer include a biochemical automatic analyzer, an automatic immune analyzer, and the like. Alternatively, the device can be mounted on a mass spectrometer used for clinical examinations, a clotting analyzer that measures clotting time of blood, or a complex system of these devices with a biochemical automatic analyzer and an automatic immune analyzer, or an automatic analysis system that applies these devices and systems.

First Embodiment

An electrolyte analyzer according to a first embodiment of the present invention will be described with reference to FIGS. 1 to 7.

First, the overall structure of the electrolyte analyzer and the configuration of main components will be described with reference to FIGS. 1 and 2. FIG. 1 is a diagram showing the overall structure of the electrolyte analyzer according to the first embodiment, and FIG. 2 is a diagram showing the schematic configuration of an analysis chamber in the electrolyte analyzer according to the first embodiment.

Figure 2:
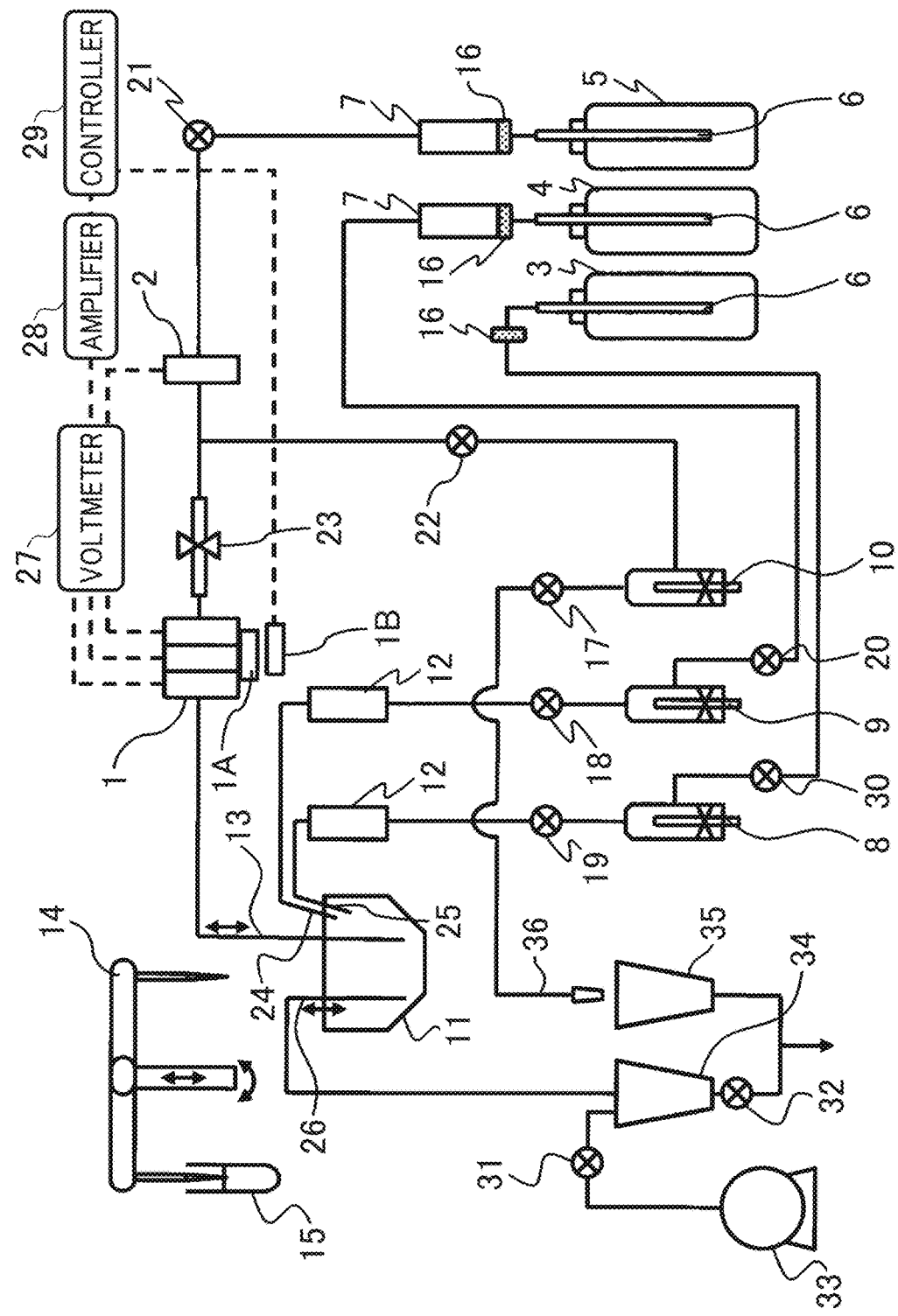
FIG. 2 is a diagram showing the schematic configuration of an analysis chamber in the electrolyte analyzer according to the first embodiment.

An electrolyte analyzer 100 shown in FIG. 2 includes a transport line 71, a gripper 55, dispensing lines 65 and 66, a pre-analysis buffer 61, a post-analysis buffer 62, two analysis chambers 50, a sample probe 14, a display device 80, a controller 29, and the like.

The transport line 71 is installed at the end part of the analyzer, and is a device that transports a transport vessel 90 mounting a plurality of sample vessels 15 accommodating a sample to a transfer position by the gripper 55, the plurality of sample vessels 15 being injected by a sample rack injection unit (not shown in the drawing), and that unloads the transport vessel 90 that ends measurement.

Note that in the present embodiment, an example is described in which the plurality of sample vessels 15 is mounted on the transport vessel 90. However, one or more sample vessels 15 only have to be mounted on the transport vessel 90. Another example of the transport vessel 90 includes a sample holder and the like that is capable of mounting one sample vessel 15.

The gripper 55 is a mechanism that transfers the transport vessel 90 from the transport line 71 to the dispensing lines 65 and 66 or from the dispensing lines 65 and 66 to the transport line 71.

The dispensing lines 65 and 66 are mechanisms that transports the sample vessel 15, which is a dispensing target, in the transport vessel 90 to a dispensing position by the sample probe 14, or that transports the transport vessel 90 accommodating the sample vessel 15 after dispensing to the post-analysis buffer 62.

The pre-analysis buffer 61 and the post-analysis buffer 62 are spaces where a sample vessel 15 waiting for dispensing to the analysis chamber 50 or a sample vessel 15 after the completion of the analysis operation wait for transportation to another place.

The analysis chamber 50 is an analysis unit having an ISE electrode 1 that measures the concentration of the electrolyte of a sample, and two analysis chambers 50 are provided, sharing the sample probe 14 that dispenses the sample to the analysis chamber 50. Referring to FIG. 2, the detail will be described. Note that the number of the analysis chambers 50 to be provided on the electrolyte analyzer 100 only has to be two or more, and the number can be three or more.

The analysis chamber 50 shown in FIG. 2 is a flow type using an ion selective electrode (in the following, which is written in the ISE electrode (Ion Selective Electrode)).

In FIG. 2, the main mechanism of the analysis chamber 50 includes five mechanisms, a sample dispensing unit, an ISE electrode unit, a reagent unit, a mechanism unit, and a waste fluid mechanism, and the controller 29 that controls these mechanisms and executes the arithmetic operation and display control of the electrolyte concentration from measurement results.

The sample dispensing unit includes the sample probe 14. With the sample probe 14, a sample such as a patient sample retained in the sample vessel 15 is dispensed and drawn into the inside of the analyzer. Here, the sample is a general term of analysis targets extracted from patient living bodies, which are blood and urine, for example. Analysis targets, which the extracted analysis targets are subjected to predetermined pre-processing, are also referred as samples.

The ISE electrode unit includes a dilution chamber 11, a sipper nozzle 13, a diluent nozzle 24, an internal standard solution nozzle 25, an ISE electrode 1, a reference electrode 2, a pinch valve 23, a voltmeter 27, and an amplifier 28. The sample dispensed by the sample dispensing unit is discharged to the dilution chamber 11, and diluted and stirred with a diluent discharged from the diluent nozzle 24 to the inside of the dilution chamber 11. The sipper nozzle 13 is connected to the ISE electrode 1 through a passage, and the diluted sample solution aspirated from the dilution chamber 11 is delivered to the ISE electrode 1 through the passage. On the other hand, the reference electrode solution accommodated in a reference electrode solution bottle 5 is delivered to the reference electrode 2 by operating the sipper syringe 10 in a state in which the pinch valve 23 is closed. The diluted sample solution delivered to the passage of the ISE electrode contacts the reference electrode solution delivered to the passage of the reference electrode, and thus the ISE electrode 1 electrically conducts the reference electrode 2. The ISE electrode unit measures the concentration of a specific electrolyte contained in the sample by the potential difference between the ISE electrode 1 and the reference electrode 2.

More specifically, the ISE electrode 1 is attached with an ion sensitive membrane having a property that electromotive force changes corresponding to the concentration of a specific ion in a sample solution (e.g. sodium ion ($Na^+$), potassium ion ($K^+$), chloride ion ($Cl^-$), and the like). The ISE electrode 1 outputs electromotive force corresponding to the concentrations of ions in the sample solution, and acquires the electromotive force between the ISE electrode 1 and the reference electrode 2 by the voltmeter 27 and the amplifier 28. The controller 29 computes the concentrations of the ions in the sample from the acquired electromotive force for display. The sample solution remaining in the dilution chamber 11 is discharged by the waste fluid mechanism.

In the present invention, the ISE electrode 1 is provided with an identification medium 1A that performs individual identification, and the ISE electrode unit includes a reader 1B that reads individual identification information recorded on this identification medium 1A. The identification information read by the reader 1B is sent to the controller 29.

In the present embodiment, the ISE electrodes 1 of the two the analysis chambers 50 analyze the same analysis item, and have the same specifications.

Note that the potential difference between the ISE electrode 1 and the reference electrode 2 has a property that is easily affected by a temperature change and the like. In order to correct potential fluctuations affected by such a temperature change and the like, the internal standard solution nozzle 25 discharges the internal standard solution to the inside of the dilution chamber 11 until the subsequent sample measurement after one sample measurement, and measurement is performed similar to the case of measuring the sample as described above. Preferably, with the use of the measurement result of the internal standard solution performed during sample measurement, correction corresponding to the amount of fluctuations is performed. Moreover, in this case, the internal standard solution is not diluted.

The reagent unit includes an aspiration nozzle 6 that aspirates a reagent from a reagent vessel, a degassing mechanism 7, and a filter 16, and supplies a reagent necessary for measurement. In the case of measuring an electrolyte, three kinds of reagents, an internal standard solution, a diluent, and a reference electrode solution, are used, and an internal standard solution bottle 3 that accommodates the internal standard solution, a diluent bottle 4 that accommodates the diluent, and the reference electrode solution bottle 5 that accommodates the reference electrode solution are set in the reagent unit. FIG. 2 shows this state. Moreover, in the case of washing the analyzer, a washing fluid bottle that stores a washing fluid is set in the reagent unit.

The internal standard solution bottle 3 and the diluent bottle 4 are respectively connected to the internal standard solution nozzle 25 and the diluent nozzle 24 via a passage through the filter 16, and the nozzles are installed with the tip end introduced into the inside of the dilution chamber 11. Moreover, the reference electrode solution bottle 5 is connected to the reference electrode 2 via a passage through the filter 16. To the passage between the diluent bottle 4 and the dilution chamber 11 and to the passage between the reference electrode solution bottle Sand the reference electrode 2, the degassing mechanism 7 is connected, and a degassed reagent is supplied to the inside of the dilution chamber 11 and the inside of the reference electrode 2. Since the pressure of the passage is reduced to a negative pressure by a syringe to aspirate the reagent from the bottle, a gas dissolved in the reagent appear as bubbles in the reagent. The degassing mechanism is provided such that the reagent including bubbles is not supplied to the dilution chamber 11 or the reference electrode 2.

Note that in the present invention, the two analysis chambers 50 are described in a form in which the reagent is supplied from the internal standard solution bottle 3, the diluent bottle 4, and the reference electrode solution bottle 5, which are used exclusively. However, a form can be provided in which one bottle is shared.

The mechanism unit includes an internal standard solution syringe 8, a diluent syringe 9, a sipper syringe 10, solenoid valves 17, 18, 19, 20, 21, 22, and 30, and a preheater 12, and responsible for the operation of liquid delivery in each mechanism or between the mechanisms, for example. For example, the internal standard solution and the diluent are delivered to the dilution chamber 11 by the operation of the internal standard solution syringe 8 and the diluent syringe 9 and the operation of the solenoid valve provided on the passage. The preheater 12 controls the temperatures of the internal standard solution and the diluent reaching the ISE electrode 1 within a certain range, and thus the influence of the temperature on the ISE electrode 1 is supposed.

The waste fluid mechanism includes a first waste fluid nozzle 26, a second waste fluid nozzle 36, a vacuum bin 34, a waste fluid receiver 35, a vacuum pump 33, and solenoid valves 31 and 32, and discharges the sample solution remaining in the dilution chamber 11 and the reaction solution remaining in the passage of the ISE electrode unit.

Returning to FIG. 1, the display device 80 is a part on which various screens such as an operation screen on which a measurement item to measure a sample to remeasured is ordered and a screen on which a measured result is confirmed, and is constituted of a liquid crystal display and the like. Specifically, a remaining measurable number management screen 501 and analysis chamber selection screens 600 and 700 shown in FIG. 4 and the like. The detail will be described later.

Note that the display device 80 does not necessarily have to be a liquid crystal display, and may be replaced by a printer and the like, may be formed of a display, a printer, and the like, or may be formed as a touch panel type display in which various parameters and settings, measurement results, measurement request information, instructions of start analysis or stop analysis, and the like are input based on a displayed operation screen.

The controller 29 is connected to the analysis chamber 50 and the like via a cable or wireless network line, and control the operation in the electrolyte analyzer 100 including the analysis chamber 50. Moreover, the controller 29 performs arithmetic operation using the potential of the ISE electrode 1 measured on the sample solution, and calculates electrolyte concentration in a sample. At this time, calibration is performed based on the potential of the ISE electrode measured on the internal standard solution, and thus it is possible to more accurately measure the electrolyte concentration.

This controller 29 can be configured of a computer including a Central Processing Unit (CPU), a Random Access Memory (RAM), a storage device, and an I/O port, and the RAM, the storage device, and the I/O port are operable to perform data exchange with the CPU. The I/O port is connected to the mechanisms described above, and controls their operation. The operation control is performed by reading a program stored in the storage device to the RAM and executing the program by the CPU. Moreover, to the controller 29, an input/output device is connected, and this enables inputs from a user and display of a measurement result.

Next, the electrolyte concentration measurement operation performed by the electrolyte measurement device shown in FIG. 2 will be described. The measurement operation is controlled by the controller 29.

First, the sample probe 14 of the sample dispensing unit discharges a sample dispensed from the sample vessel 15 to the dilution chamber 11 of the ISE electrode unit. After the sample is dispensed to the dilution chamber 11, a diluent is discharged out of the diluent bottle 4 from the diluent nozzle 24 by the operation of the diluent syringe 9 to dilute the sample. As described above, in order to prevent bubbles from occurring due to the temperature of the diluent in the passage or a change in the pressure, the degassing mechanism 7 mounted in the midway point of the passage of the diluent performs a degassing process. The diluted sample solution is aspirated to the ISE electrode 1 by the operation of the sipper syringe 10 or the solenoid valve 22.

On the other hand, by the pinch valve 23 and the sipper syringe 10, the reference electrode solution is delivered to the inside of the reference electrode 2 from the reference electrode solution bottle 5. The reference electrode solution is a potassium chloride (KCl) aqueous solution at a predetermined concentration, for example, and the sample solution contacts the reference electrode solution to electrically conduct the ISE electrode 1 with the reference electrode 2. Note that the electrolyte concentration of the reference electrode solution is desirably a high concentration in order to suppress the influence of the concentration of fluctuations during the delivery of the sample. However, since there is a possibility of a cause of crystallization and clogging near saturation concentration, desirably, the concentration ranges from 0.5 mmol/L to 3.0 mmol/L. The potential of the ISE electrode based on the potential of the reference electrode is measured using the voltmeter 27 and the amplifier 28.

Moreover, the internal standard solution of the internal standard solution bottle 3 set before and after sample measurement on the reagent unit is discharged to the dilution chamber 11 by the internal standard solution syringe 8, and the measurement of the electrolyte concentration of the internal standard solution is performed similarly to the sample measurement.

Figure 3:
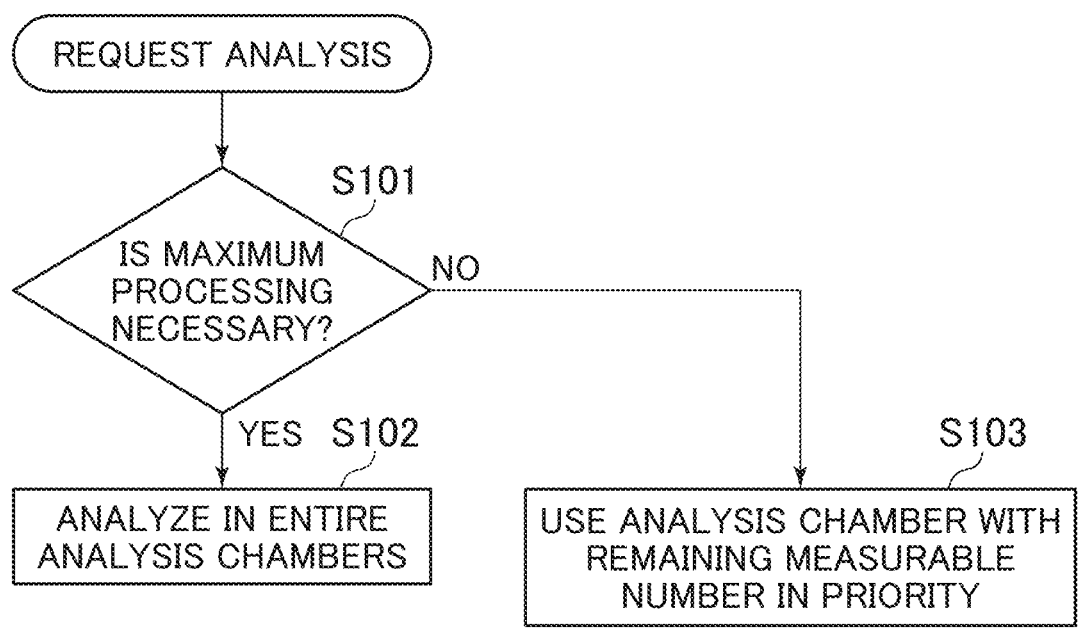
FIG. 3 is a determination flow of request status and processing performance in the electrolyte analyzer according to the first embodiment.
Figure 5:
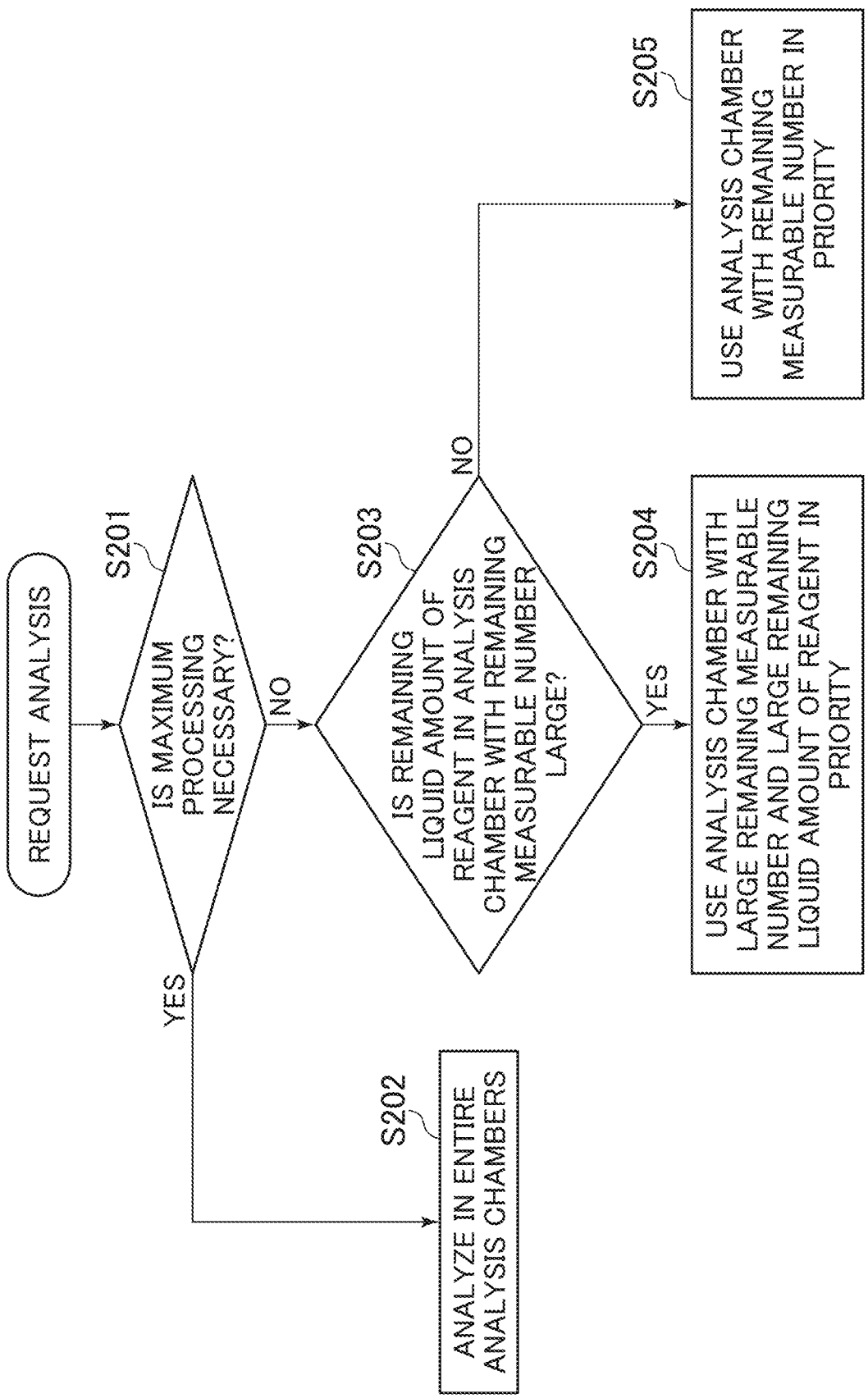
FIG. 5 is another example of a determination flow of request status and processing performance in the electrolyte analyzer according to the first embodiment.
Figure 6:
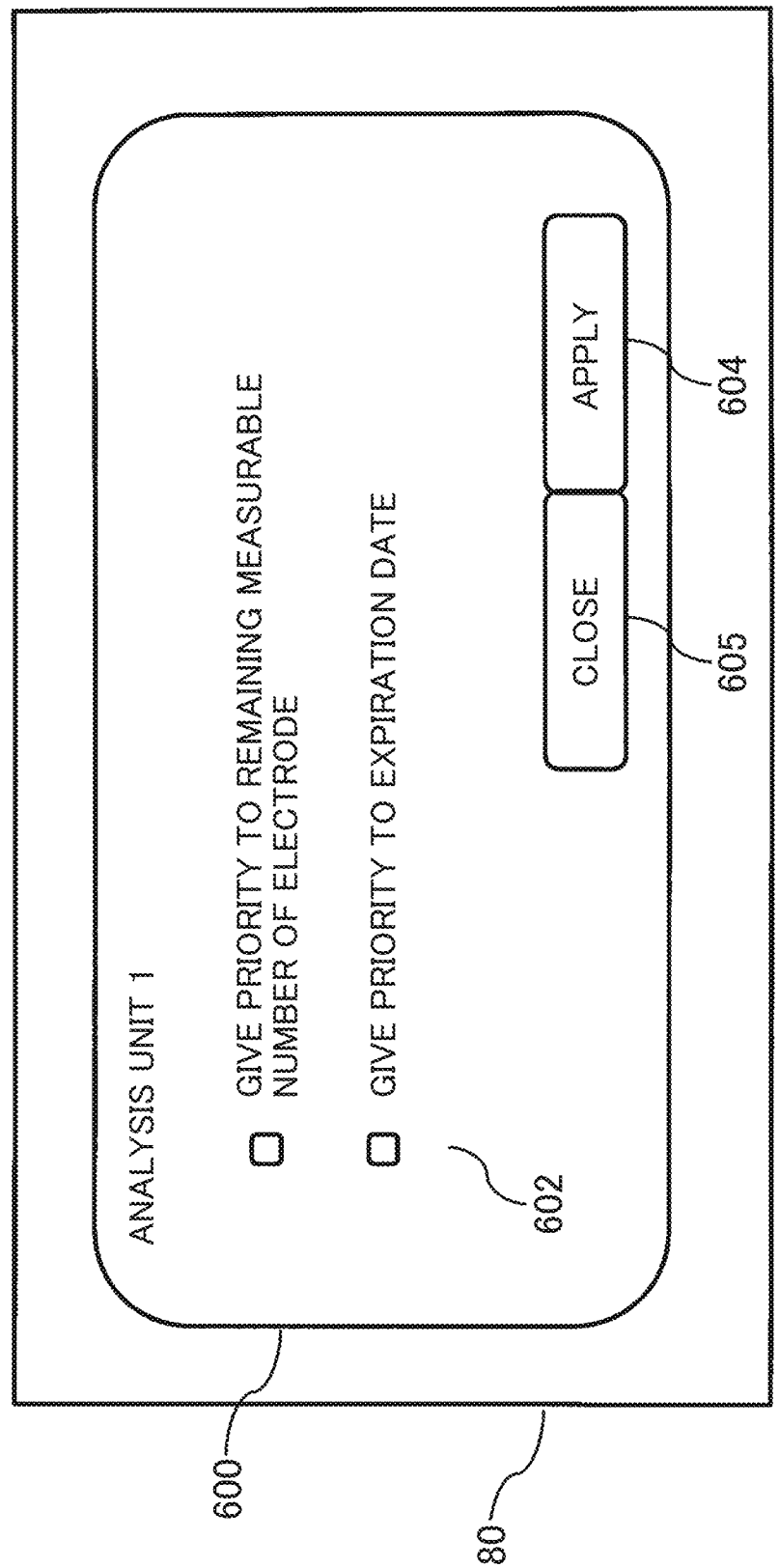
FIG. 6 is a diagram showing a screen that is displayed on the display device of the electrolyte analyzer according to the first embodiment and that selects an analysis chamber used in priority.

Next, the detail of control and procedures that allocate analysis to a plurality of analysis chambers 50 according to the present invention will be described with reference to FIGS. 3 to 7. FIGS. 3 and 5 show a determination flow of request status and processing performance, FIG. 4 is a diagram showing a screen that manages remaining measurable numbers displayed on the display device, FIGS. 6 and 7 are diagrams showing a screen that is displayed on the display device and that selects an analysis chamber used in priority.

In the present embodiment, when the analysis of a sample is instructed from the input unit of the controller 29 or the operation screen of the display device 80, the controller 29 selects the analysis chamber 50 to be used for measurement from the two analysis chambers 50 corresponding to the remaining measurable numbers and the measurement request status of the ISE electrodes 1 of the two analysis chambers 50.

For example, in the case in which it is determined that the number of measurement requests processed by the electrolyte analyzer 100 within a predetermined time period is less than the maximum processing performance, allocation is performed such that the analysis chamber 50 having a largest remaining measurable number is used in priority. At this time, in addition to or instead of the remaining measurable numbers, allocation can be performed using the valid expiration date of the ISE electrode 1. Note that in this case, Step S203 in FIG. 6, described later, is replaced by the step of "determining whether the valid expiration date of the ISE electrode 1 of the analysis chamber 50 having a large remaining measurable number is longer than the other analysis chamber 50."

Here, in the present embodiment, desirably, the controller 29 manages the remaining measurable numbers based on individual identification information read by the reader 1B.

Such a determination flow will be described with reference to FIG. 3.

First, when it is determined that an analysis request is arrived, the controller 29 determines whether the maximum processing is necessary (Step S101). When it is determined that the maximum processing is necessary, the process goes to Step S102, and analysis is executed in all the analysis chambers 50 (Step S102). In contrast to this, when it is determined that the maximum processing is unnecessary, the process goes to Step S103, and the analysis chamber 50 having a large remaining measurable number is used in priority (Step S103).

More specifically, the maximum processing performances of the analysis chambers 50 are set to 300 samples/hour, i.e., 5 samples/minute. Under such conditions, in the case in which the number of samples that have to be processed for two minutes exceeds 20 samples, i.e., 5 samples/(minute×chamber)×two chambers×two minutes, allocation is performed such that both of the two analysis chambers 50 perform processing at the maximum performance.

Moreover, in the case in which the number of samples that have to be processed for two minutes is 15 samples and the remaining measurable number of one of the analysis chambers 50 is smaller, when no control is performed, the allotment is 8:7 and the like, whereas in the present embodiment, the analysis chamber 50 having a large remaining measurable number is to perform the maximum processing (ten measurements), and the analysis chamber 50 having a smaller remaining measurable number is to analyze only five measurements. Note that in the case in which the remaining measurable numbers are almost the same and the like, allotment is equal.

Further, in the case in which a request is a single analysis request and the remaining measurable number of one of the analysis chambers 50 is small, the analysis operation of the analysis chamber 50 having a large remaining measurable number is to be performed.

In the execution of such control, in order that the user can grasp the status of the remaining measurable numbers and the like of the analysis chambers 50, desirably, the remaining measurable number management screen 501 shown in FIG. 4 is displayed on the display device 80.

The remaining measurable number management screen 501 shown in FIG. 4 is a screen displayed on the display device 80 displaying a chamber display region 503 on which the type of the target analysis chamber 50, a species display region 504 on which the types of ion sensitive membranes are displayed in the ISE electrode 1, a remaining measurement number display region 505 on which the remaining measurement numbers of the ion sensitive membranes are displayed, an expiration date display region 506 on which the expiration date of the ion sensitive membranes is displayed, and a close button 508 that is pressed down when the remaining measurable number management screen 501 is closed. According to such screens, the user can easily grasp which state the analysis chambers 50 presently are.

Moreover, in the present embodiment, in addition to the remaining measurable numbers, desirably, the controller 29 selects the analysis chamber 50 used for measurement also based on the remaining liquid amount of the reagent used in the analysis chamber 50.

For example, an analysis plan is allocated such that the analysis chamber 50 having a large remaining measurable number (the remaining liquid amount or the remaining measurement number) of the reagent is used in priority as well as the remaining measurable number of the ISE electrode 1. Since the initial capacities of the internal standard solution bottle 3, the diluent bottle 4, and the reference electrode solution bottle 5 are known, the remaining measurable number of the reagent can be found by subtracting, from the initial capacity, the used amount that is the number of times of the bottle used for analyzes×one time.

In this case, as shown in FIG. 5, first, when it is determined that an analysis request is arrived, the controller 29 determines whether the maximum processing is necessary (Step S201). When it is determined that the maximum processing is necessary, the process goes to Step S202, and analysis is executed in all the analysis chambers 50 (Step S202). In contrast to this, when it is determined that the maximum processing is unnecessary, the process goes to Step S203, and it is determined whether the remaining liquid amount of the reagent of the analysis chamber having a large remaining measurable number is large (Step S203). When it is determined as large, the analysis chamber 50 having a large remaining measurable number with a large remaining liquid amount is used in priority (Step S204). In contrast to this, it is not determined as large, the analysis chamber 50 having a large remaining measurable number is used in priority at an allotment about at intermediate in the case in which allotment is equal to the allotment in Step S204 (Step S205).

Moreover, desirably, in addition to the remaining measurable numbers, the controller 29 selects the analysis chamber 50 used for measurement also based on the sample holding number of the post-analysis buffer 62.

For example, in the case in which it can be determined that samples pile up in the post-analysis buffer 62 when analysis is performed at the maximum processing performance under the conditions where the samples remain in the post-analysis buffer 62 and the electrolyte analysis continues, processing performance is temporarily dropped to smooth the analysis chambers 50 corresponding to the remaining measurable numbers. Moreover, in the case in which samples remain in the pre-analysis buffer 61 and a request for the analysis of the sample is further input, both the analysis chambers 50 can perform the maximum processing. Note that in this case, Step S203 in FIG. 5 is replaced by the step of "determining whether the sample holding number of the post-analysis buffer is a predetermined amount or more."

Further, desirably, the user can select the analysis chamber 50 to be used in priority.

For example, the analysis chamber selection screen 600 shown in FIG. 6 is a screen that selects whether priority is given to the maximum processing number or priority is given to the expiration date, a check box 602 of an item to which priority is given is checked to press down an apply button 604 for application. When the analysis chamber selection screen 600 is closed, a close button 605 is pressed down.

Moreover, the analysis chamber selection screen 700 shown in FIG. 7 is a screen that selects the analysis chamber 50 with analysis in priority for execution by the user, as a basis for determination whether to give priority, displaying status on a chamber display region 703 on which the type of the target analysis chamber 50 is displayed, an electrode remaining measurable number display region 704 on which the remaining measurement numbers of the ion sensitive membranes is displayed, an expiration date display region 705 on which the expiration date of the ion sensitive membrane is displayed, and a reagent state display region 706 on which the remaining measurable numbers of the reagents and their expiration date are displayed. The user checks a check box 702 based on the numerical value to be displayed, and presses down an apply button 707 for application. When the analysis chamber selection screen 700 is closed, a close button 708 is pressed down.

According to such analysis chamber selection screens 600 and 700, measures are possible in the case in which all consumable items are desired to be used quickly corresponding to the intention of the user while maintaining processing performance. Furthermore, this is also effective in the case in which the ISE electrode 1 or the reagent has a usable (valid) date except the remaining measurable numbers and the designated analysis chamber 50 is used in priority to quickly use all consumable items having a short expiration date.

Next, the effect of the present embodiment will be described.

The above-described electrolyte analyzer 100 according to the first embodiment of the present invention includes a plurality of analysis chambers 50 having the ISE electrode 1 that measures the concentration of the electrolyte of the sample and the controller 29 that controls the operation in the electrolyte analyzer 100 including the analysis chamber 50. The ISE electrodes 1 of the plurality of analysis chambers 50 analyze the equal analysis item. The controller 29 selects the analysis chamber 50 used for measurement from the plurality of analysis chambers 50 corresponding to the remaining measurable numbers and the measurement request status of the plurality of the ISE electrodes 1.

In the conventional case, measurement can continue with no use of the analysis chamber 50 with the remaining measurable number, which is zero. However, there is a demerit that fails to maintain the maximum processing performance due to a reduction in the number of the analysis chambers 50. In contrast to this, for example, the analysis chamber 50 to be used is selected corresponding to the remaining measurable numbers, it is possible to give priority to maintaining processing performance when the analysis request status is close to the maximum processing performance to perform the analysis operation. Moreover, in the case in which the request status is intermitted, it is possible to equalize the remaining measurable number of times of the plurality of analysis chambers 50 with the use of the analysis chamber 50 having a large remaining measurable number in priority. As described above, since the user can adjust the timing of replacing consumable items, it is possible to replace consumable items at appropriate timing s compared with the conventional case, and it is possible to sufficiently exert the analysis performances of the analysis chambers 50.

Furthermore, in the case in which the controller 29 determines that the number of measurement requests processed by the electrolyte analyzer 100 within a predetermined time period is less than the maximum processing performance, the analysis chamber 50 having a largest remaining measurable number is used in priority, and the maximum processing performance s maintained when necessary whereas the remaining measurable numbers are smoothed when unnecessary. Thus, it is possible to perform analysis also in consideration of the replacement of consumable items while further utilizing the analysis processing performance of the analyzer.

Further, the controller 29 selects the analysis chamber 50 used for measurement also based on the remaining liquid amount of the reagent used in the analysis chamber 50 in addition to the remaining measurable numbers, and thus it is possible to adjust the replacement frequencies of consumable items in including the reagent, and it is possible to intend to replace consumable items at timing in convenience for the user. For example, it is possible to adjust the replacement of the ISE electrode 1 and the reagent bottle to close and shorten the timing when analysis has to be stopped as short as possible.

Moreover, the post-analysis buffer 62 that transports the sample vessel 15 after the completion of the analysis operation to another place is further included. The controller 29 selects the analysis chamber 50 used for measurement also based on the sample holding number of the post-analysis buffer 62 in addition to the remaining measurable numbers. Thus, it is possible to determine processing performance adding the sample transport performance, and it is possible to execute more suited for the actual operation of the analyzer while appropriately performing smoothing the replacement frequency of consumable items.

Further, the ISE electrode 1 has the identification medium 1A that performs individual identification, and further includes the reader 1B that reads individual identification information recorded on the identification medium 1A. The controller 29 manages the remaining measurable numbers based on the individual identification information read by the reader 1B, and thus it is possible to automatically execute determination of the remaining measurable numbers on the analyzer side.

Second Embodiment

Figure 8:
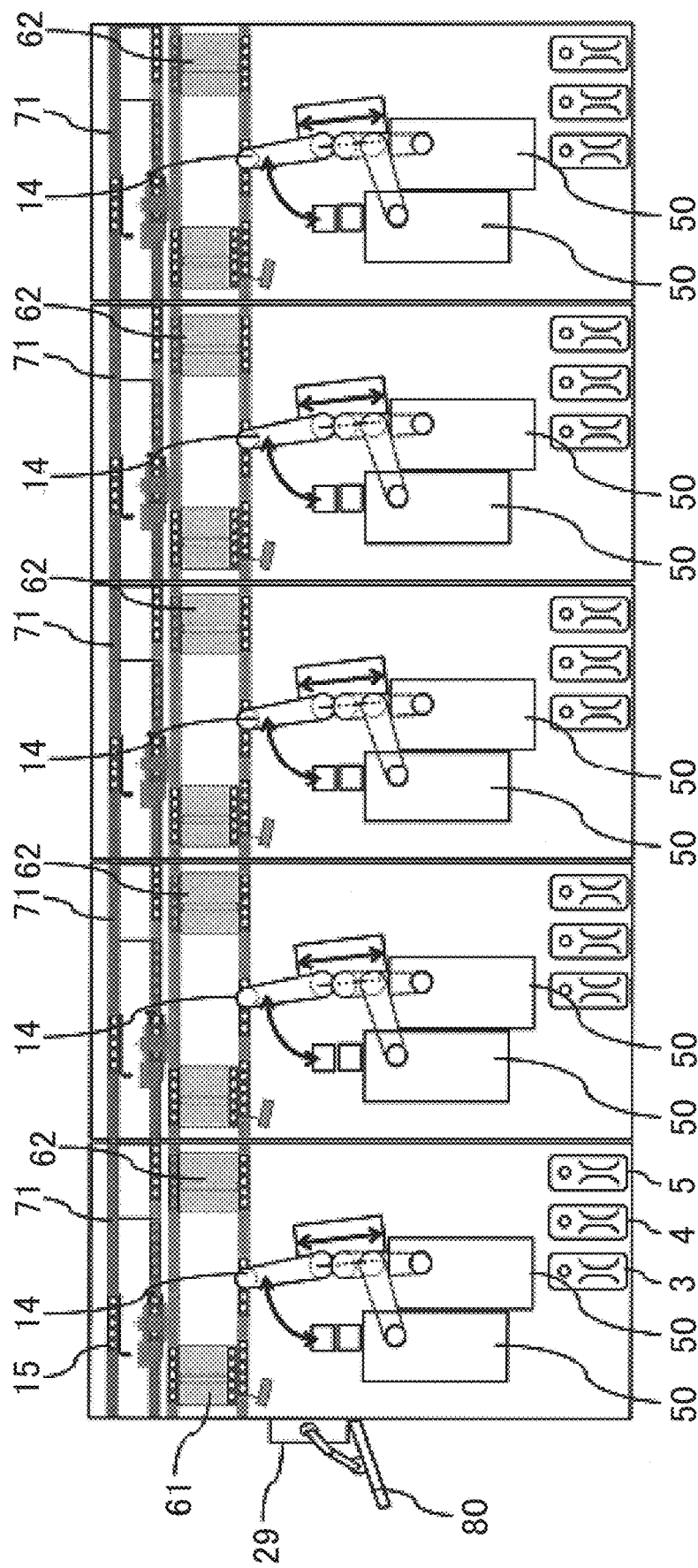
FIG. 8 is a diagram showing the overall structure of an electrolyte analyzer according to a second embodiment of the present invention.

An electrolyte analyzer according to a second embodiment of the present invention will be described with reference to FIGS. 8 to 10. FIG. 8 is a diagram showing the overall structure of the electrolyte analyzer according to the second embodiment, and FIGS. 9 and 10 are diagrams showing a screen that is displayed on the display device of the electrolyte analyzer and that selects a dispensing mechanism used in priority.

An electrolyte analyzer 100A of the present second embodiment shown in FIG. 8 has a configuration in which in the electrolyte analyzer 100 shown in FIG. 2, a configuration of the controller 29 and the display device 80 and five configurations related to a unit including the two analysis chambers 50 and transport are included. In the configuration shown in FIG. 8, the number of the analysis chambers 50 provided in the unit for analysis is not necessarily two, which can be one or three or more.

In such an electrolyte analyzer 100A, a controller 29 selects a sample probe 14 to be used for dispensing or an analysis chamber 50 used for measurement that is the subsequent stage corresponding to the remaining measurable numbers and the of measurement request status of a plurality of analysis chambers 50.

For example, a selection can be made whether among five sample probes 14, any of the five sample probes 14 is used for dispensing, i.e., analysis can be performed in any of the analysis units.

Moreover, in the execution of such control, a dispensing mechanism selection screen 800 shown in FIG. 9 can be used.

The dispensing mechanism selection screen 800 shown in FIG. 9 is a screen that indirectly selects an analysis unit having an analysis chamber 50 that executes analysis in priority by a user by selecting a sample probe 14. As a basis for determination whether to give priority, status is displayed on a dispensing mechanism selection region 802 on which the type of an analysis unit that is a target, an electrode remaining measurable number display region 803 on which the remaining measurement numbers of an ion sensitive membranes is displayed, an expiration date display region 804 on which the expiration date of the ion sensitive membrane is displayed, a reagent remaining measurable number display region 805 on which the remaining measurable numbers of reagents is displayed, and a reagent expiration date display region 806 on which the expiration date of the reagents is displayed. The user selects the corresponding analysis unit of the dispensing mechanism selection region 802 based on the numerical value to be displayed to press down an apply button 807 for application. When the dispensing mechanism selection screen 800 is closed, a close button 808 is pressed down.

Further, as shown in FIG. 9, the analysis unit used in priority for analysis, which is an analysis unit 4 in FIG. 9, can be displayed with a highlight.

Moreover, among ten analysis chambers 50 in total, a selection can be made whether to give priority to any analysis chamber 50. In this case, the number of selectable analysis chamber 50 is not limited specifically, which can be two or more.

An analysis chamber selection screen 900 shown in FIG. 10 is a screen that selects the analysis chamber 50 with analysis in priority for execution by the user, as a basis for determination whether to give priority, displaying status on a chamber selection region 902 on which the type of the target analysis chamber 50 is displayed, an electrode remaining measurable number display region 903 on which the remaining measurement numbers of the ion sensitive membranes is displayed, an expiration date display region 904 on which the expiration date of an ion sensitive membrane is displayed, a reagent remaining measurable number display region 905 on which the remaining measurable numbers of reagents is displayed, and a reagent expiration date display region 906 on which the expiration date of the reagent is displayed. The user selects the corresponding analysis unit of the chamber selection region 902 based on the numerical value to be displayed to press down an apply button 907 is pressed down for application. When the analysis chamber selection screen 900 is closed, a close button 908 is pressed down.

Further, similarly to FIG. 9, the analysis units used in priority for analysis, which are an analysis chamber 1 of an analysis unit 2, an analysis chamber 2 of an analysis unit 3, and an analysis chamber 1 of an analysis unit 4 in FIG. 10, can be displayed with a highlight.

The other configurations and operations are almost the same configurations and operations as the electrolyte analyzer of the foregoing first embodiment, and the detail is omitted.

Also in the electrolyte analyzer according to the second embodiment of the present invention, the effects almost similar to those of the electrolyte analyzer according to the foregoing first embodiment can be obtained.

Moreover, the plurality of analysis chambers 50 shares the sample probe 14 that dispenses a sample to the analysis chamber 50. In the case of including a plurality of sample probes 14, the controller 29 selects the sample probe 14 to be used for dispensing and the analysis chamber 50 used for measurement corresponding to the remaining measurable numbers and the of measurement request status of the plurality of analysis chambers 50, and thus it is possible to optimize a module to be used corresponding to the remaining measurable numbers of consumable items in units of a module. Accordingly, also in the entire system, management is possible such as unifying the replacement frequency (or divided into two systems).

Others

Note that the present invention is not limited to the foregoing embodiments, which includes various exemplary modifications. The foregoing embodiments have been described ion detail for easily understanding the present invention, which are not necessarily limited to those having all the described configurations.

Moreover, a part of the configuration of an embodiment may be replaced by the configuration of another embodiment, and the configuration of another embodiment may be added to the configuration of an embodiment. Furthermore, in regard to a part of the configuration of the embodiments, another configuration may be added, removed, or replaced.

REFERENCE SIGNS LIST

1: ISE electrode (consumable item)
1A: identification medium
1B: reader
2: reference electrode
3: internal standard solution bottle
4: diluent bottle
5: reference electrode solution bottle
6: aspiration nozzle
7: degassing mechanism
8: internal standard solution syringe
9: diluent syringe
10: sipper syringe
11: dilution chamber
12: preheater
13: sipper nozzle
14: sample probe (dispensing mechanism)
15: sample vessel
16: filter
17, 18, 19, 20, 21, 22, 30, 31, 32: solenoid valve
23: pinch valve
24: diluent nozzle
25: internal standard solution nozzle
26: first waste fluid nozzle
27: voltmeter
28: amplifier
29: controller (control unit)
33: vacuum pump
34: vacuum bin
35: waste fluid receiver
36: second waste fluid nozzle
50: analysis chamber
55: gripper
61: pre-analysis buffer
62: post-analysis buffer
65, 66: dispensing line
71: transport line
80: display device
90: transport vessel
100, 100A: electrolyte analyzer
501: remaining measurable number management screen
503, 703: chamber display region
504: species display region
505: remaining measurement number display region
506, 705, 804, 904: expiration date display region
508, 605, 708, 808, 908: close button
600, 700, 900: analysis chamber selection screen
602, 702: heck box
604, 707, 807, 907: apply button
704, 803, 903: electrode remaining measurable number display region
706: reagent state display region
800: dispensing mechanism selection screen
802: dispensing mechanism selection region
805, 905: reagent remaining measurable number display region
806, 906: reagent expiration date display region
902: chamber selection region

What is claimed is:

1. An electrolyte analyzer that analyzes electrolyte concentration of a sample, the electrolyte analyzer comprising:
a plurality of analysis chambers having consumable items that measure a concentration of an electrolyte of the sample; and
a control unit configured to control operations in the electrolyte analyzer including the analysis chamber,
wherein the plurality of analysis chamber share a dispensing mechanism configured to dispense the sample to the analysis chamber,
wherein the consumable items of the plurality of analysis chambers analyze equal analysis items,
wherein the control unit is configured to select an analysis chamber used for measurement from the plurality of analysis chambers corresponding to remaining measurable numbers of the plurality of consumable items and measurement request status, and
wherein when a plurality of the dispensing mechanisms is included, the control unit is configured to select the dispensing mechanism used for dispensing and the analysis chamber used for measurement corresponding to remaining measurable numbers and measurement request status of the plurality of analysis chambers.

2. The electrolyte analyzer according to claim 1,
wherein the control unit is configured such that when it is determined that a number of measurement requests to be processed within a predetermined time period by the electrolyte analyzer is less than a maximum processing performance, the control unit uses an analysis chamber having a largest remaining measurable number in priority.

3. The electrolyte analyzer according to claim 1,
wherein the control unit is configured to select the analysis chamber used for measurement also based on a remaining liquid amount of a reagent used in the analysis chamber in addition to the remaining measurable number.

4. The electrolyte analyzer according to claim 1, further comprising:
a sample buffer unit configured to transport a sample vessel after completion of analysis to another place,
wherein the control unit is configured to select the analysis chamber used for measurement also based on a sample holding number of the sample buffer unit.

5. The electrolyte analyzer according to claim 1,
wherein the consumable item has an identification medium for identification,
wherein a reader configured to read identification information recorded on the identification medium is further included, and
wherein the control unit is configured to manage the remaining measurable number based on the identification information read at the reader.

6. The electrolyte analyzer according to claim 1,
wherein the control unit is configured to display a selection screen that selects the analysis chamber used for measurement.

7. The electrolyte analyzer according to claim 6,
wherein the control unit is configured to display a remaining measurable number and an expiration date in the selection screen.

* * * * *